United States Patent [19]

Yamamoto et al.

[11] Patent Number: 5,663,460
[45] Date of Patent: Sep. 2, 1997

[54] LIQUID L-N-MENTHOL COMPOSITION AND PROCESS FOR PREPARING THE SAME

[75] Inventors: Takeshi Yamamoto; Hideaki Ohta, both of Kanagawa, Japan

[73] Assignee: Takasago International Corporation, Tokyo, Japan

[21] Appl. No.: 506,983

[22] Filed: Jul. 28, 1995

[30] Foreign Application Priority Data

Jul. 29, 1994 [JP] Japan .................................. 6-196279
Jun. 26, 1995 [JP] Japan .................................. 7-180566

[51] Int. Cl.$^6$ .................................................. C07C 35/12
[52] U.S. Cl. ................................... 568/829; 568/828
[58] Field of Search .................................. 568/829, 828

[56] References Cited

U.S. PATENT DOCUMENTS

| | | | |
|---|---|---|---|
| 4,237,072 | 12/1980 | Aviron-violet et al. | 568/459 |
| 5,227,163 | 7/1993 | Elini et al. | 424/195.1 |
| 5,230,897 | 7/1993 | Griffin et al. | 424/449 |

OTHER PUBLICATIONS

Imaizumi et al., "Effects of Essential . . . Rats", Agric. Biol. Chem., vol. 49(9), pp. 2795–2796. Sep. 1985.
Chang et al., "Vapor–phase . . . Monoterpenes", Agr. Biol. Chem., vol. 34(11), pp. 1734–1738. Nov. 1970.

*Primary Examiner*—José G. Dees
*Assistant Examiner*—Rosalynd Williams
*Attorney, Agent, or Firm*—Sughrue, Mion, Zinn, Macpeak & Seas

[57] ABSTRACT

A liquid l-n-menthol composition containing 30 to 80% by weight of (−)-n-isopulegol and a process for preparing a liquid l-n-menthol composition comprising mixing 20 to 70 parts by weight of liquid menthol at a temperature of not lower than 42° C. as obtained in the production of l-n-menthol with 30 to 80 parts by weight of (−)-n-isopulegol are disclosed. Further, the liquid l-n-menthol composition in which part of the (−)-n-isopulegol is replaced with 3-l-n-menthoxypropane-1,2-diol and the process for preparing the same are also disclosed. The liquid l-n-menthol composition of the present invention is less expensive than conventionally available menthol and yet has an improved feeling of coolness (particularly, the bitterness is reduced) and can be used in place of conventional menthol. Besides, the liquid menthol composition of the present invention is excellent in workability and hygiene on use. Further, by replacing part of the (−)-n-isopulegol component with 3-l-n-menthoxypropane-1,2-diol, both the odor of menthol and the irritation on the skin by menthol can be softened, and the feeling of mildness can be more increased.

6 Claims, No Drawings

LIQUID L-N-MENTHOL COMPOSITION AND PROCESS FOR PREPARING THE SAME

FIELD OF THE INVENTION

This invention relates to a liquid l-n-menthol composition which renders l-n-menthol be made use of more economically and effectively and to a process for preparing the composition.

BACKGROUND OF THE INVENTION l-n-Menthol has been widely used as a cooling agent on the world-wide scale of thousands of tons per year in drugs, toothpaste, tobacco, chewing gum, confectionery, beverages, cosmetics, etc.

Natural l-n-menthol can be obtained by cooling peppermint oil obtained by steam distillation of Japanese peppermint (*Mentha arvensis*) and recrystallizing the precipitated l-n-menthol from peppermint white oil as a solvent. Processes currently adopted for synthesizing l-n-menthol on an industrial scale include a process starting with d-citronellal (Takasago process; see Indo Motoichi, *Koryo*, No. 177, pp 33–47 (1993)) and a process starting with thymol (Haarman Reimer GMBH DE).

Since l-n-menthol has a melting point of 42° to 44° C. and is solid at room temperature, synthetic l-n-menthol products for the market are prepared by distilling crude l-n-menthol, flaking the resulting liquid l-n-menthol having a temperature above the melting point in a flaking machine, and packaging the resulting flaky menthol usually in 50 l-volume fibre-drums. However, the loss of menthol due to sublimation during packaging reaches 2%, and the poor workability in this packaging operation increases the cost of commercialization. Additionally, the form of the package and the small bulk density of the flakes also increase the cost of packaging and transportation. All these factors have increased the cost of menthol.

On the other hand, handling of flaky menthol involves a problem of working environment. That is, workers on flakes of menthol are to be exposed to highly concentrated menthol vapor, which would be too strong irritation in long-time working.

Further, it has been pointed out that menthol flakes are apt to cake partly when preserved at high humidity and high temperature (below the melting point, e.g., 25° to 35° C.) for a long time, and cases are sometimes met with in which a user finds the product no more usable practically. Therefore, the development of the process for improving these problems has been desired.

SUMMARY OF THE INVENTION

An object of the present invention is to provide l-n-menthol in the form of a liquid composition for commercial use which can be prepared without involving flaking.

Another object of the present invention is to provide a process for preparing the liquid composition of l-n-menthol.

As a result of extensive investigations, the present inventors have found that a composition consisting of 70% by weight or less of l-n-menthol and at least 30% by weight of isopulegol which is structurally similar to menthol completely keeps a liquid state even at 25° C. They have also found that incorporation of both optically and chemically pure odorless l(−)-n-isopulegol into menthol provides a liquid menthol composition without impairing the well-known feeling of coolness of menthol. To their surprise, this composition suppresses the bitterness of menthol and, when used in oral care products, produces enhanced effects over menthol per se. The present invention has been completed based on these findings.

The present invention provides (1) a liquid l-n-menthol composition containing 30 to 80% by weight of (−)-n-isopulegol, (2) a liquid l-n-menthol composition according to (1) above, wherein part of the (−)-n-isopulegol component is replaced with 3-l-n-menthoxypropane-1,2-diol, (3) a liquid l-n-menthol composition according to (1) or (2) above, wherein the (−)-n-isopulegol is obtained by deep cooling in a solvent mainly comprising acetone, (4) a process for preparing a liquid l-n-menthol composition comprising mixing 20 to 70 parts by weight of liquid menthol having a temperature of not lower than 42° C. with 30 to 80 parts by weight of (−)-n-isopulegol, and (5) a process for preparing a liquid l-n-menthol composition according to (4) above, wherein part of the (−)-n-isopulegol component is replaced with 3-l-n-menthoxypropane-1,2-diol.

DETAILED DESCRIPTION OF THE INVENTION (−)-n-Isopulegol which is used in the present invention is described below in detail.

Isopulegol has three asymmetric carbon atoms and includes four geometric isomers (n-form, neo-form, iso-form, and neoiso-form) and eight optical isomers.

Of these isomers, (−)-n-isopulegol is industrially prepared by cyclization of (+)-citronellal. (+)-Citronellal having an optical purity of 80 to 85%e.e. which is obtained from citronella oil has conventionally been used as the starting material but recently has been replaced with optically purer (+)-citronellal (optical purity: 97.5%e.e.; see Indo Motoichi, *Koryo* (*Perfumery*), No. 177, pp 33–47 (1993)) which is obtained by asymmetric isomerization of geranyl diethylamine using an Rh-BINAP complex catalyst (Rh complex having 2,2'-bis(diphenylphosphino)-1,1'-binaphthyl as a ligand).

It is known that cyclization of (+)-citronellal is carried out by using silica gel (U.S. Pat. No. 3,218,361), zeolite (*Applied Catalyst*, Vol. 47, pp. 367–374 (1989)), a rhodium complex (*Chem. Pharm. Bull.*, Vol. 37, pp. 1990–1994 (1989) and *Tetrahedron Lett.*, pp. 4375–4376 (1972)), a copper-chromium catalyst (*Bull. Chem. Soc. Jap.*, Vol. 41, pp. 2530–2532 (1968)), an alkylaluminum chloride (*J. Am. Chem. Soc.*, Vol. 102, pp. 7951–7953 (1980)), a solid acid-base catalyst (*Chem. Lett.*, Vol. 10, pp. 1797–1798 (1989)), or zinc bromide [JP-B-59-45661 (the term "JP-B" as used herein means an examined Japanese patent publication), and *Synthesis*, Vol. 2, pp. 147–148 (1978)]. Of these cyclization processes, the process of using silica gel has hitherto been of frequent use, while the process of using zinc bromide has recently been replacing for the high selectivity to the (−)-n-compound.

Isopulegol mainly composed of the (−)-n-compound has a minty herbaceous and bitter sweet fragrance and gives off a bitter but sharp note at a concentration of 50 ppm or higher and a herbaceous bitter note or a bitter sweet and minty note at a concentration of about 10 ppm. In the field of perfumery, it has been added to a perfume composition in a small amount for the purpose of lifting a rose note, a geranium note, a reseda note, an oriental note, a tuberose note, etc. (Arctander, *Perfume and Flavor Chemicals*, Compound No. 2768). With respect to a feeling of coolness of (−)-n-isopulegol, Yamazaki Hisaichi, et al. report in *Koryo* (*Perfumery*), No. 95, pp. 39–43 (1993) that (−)-n-isopulegol slightly gives a feeling of coolness. There is also an unexamined published Japanese patent application (Nakagawa Akira, et al., JP-A-6-65023) disclosing applicability of (−)-n-isopulegol as an agent for giving a feeling of coolness.

As previously described, isopulegol that has conventionally been used as a perfume component is a mixture of the eight optical isomers mainly comprising (−)-n-isopulegol which is synthesized by cyclization of (+)-citronellal obtained from citronella oil and having an optical purity of 80 to 85%e.e. (d-form: 90 to 92.5%; l-form: 10 to 7.5%) or (+)-citronellal obtained by asymmetric isomerization of geranyl diethylamine using an Rh-BINAP catalyst and having an optical purity of 97.5 to 98%e.e. (d-form: 98.75 to 99%; l-form: 1.25 to 1.0%).

The above-described isopulegol mixture obtained in menthol synthesis as an intermediate can be purified by deep cooling in a petroleum hydrocarbon, followed by recrystallization once or twice to give (−)-n-isopulegol having an optical purity of not lower than 99%e.e. and a chemical purity of 99 to 99.5% by weight. The thus purified compound still has a relatively mild, minty herbaceous, and bitter sweet scent and can be used as a perfume component.

When a liquid l-n-menthol composition containing not less than 30% of the above-mentioned (−)-n-isopulegol having an optical purity of not lower than 99%e.e. and a chemical purity of 99 to 99.5% by weight was experimentally prepared and evaluated, it was found that the composition is excellent in feeling of coolness on the skin or in the mouth but masks the cooling odor possessed by menthol and thus cannot be used in place of menthol.

There are reports on optically pure (−)-n-isopulegol obtained by, for example, repeated recrystallization in petroleum ether (P & E. O.R., p. 365 (1968); $[\alpha]_D^{20} = -31.70°$) or recrystallization of a magnesium salt of isopulegol phthalate (J. Chem. Soc., p. 1248 (1920)), but no mention of the fragrance of the thus purified compound is made in the reports.

Attempting to examine the fragrance of optically and chemically pure (−)-n-isopulegol, the inventors of the present invention further purified the above-mentioned (−)-n-isopulegol having an optical purity of not lower than 99%e.e. and a chemical purity of 99 to 99.5% by weight by cooling at −30° to −35° C. while stirring in twice (vol/wt) as much petroleum ether as the isopulegol, separating the precipitated crystals by centrifugation, and repeating the same operation (deep cooling) six times to obtain (−)-n-isopulegol having a chemical purity of 100% by weight and an optical purity of 100%e.e. ($[\alpha]_D^{25} = -22.1°$). As a result, it was surprisingly revealed that 100% pure (−)-n-isopulegol is completely odorless, giving off no minty and herbaceous odor which has hitherto been considered essential to isopulegol, but only gives refreshing irritation with a feeling of coolness.

In order to identify the perfuming components of the unpurified (−)-n-isopulegol, the mother liquor was subjected to precise fractional distillation (rectification) on a 40-plate Heli-Pack distillation tower. Gas chromatography (GC) of the distillate lent confirmation to the presence of impurities (0.3% by weight) which are by-produced in cyclization of citronellal, such as 3,8-paramenthadiene, 2,8-paramenthadiene, 3-methylcyclohexanol, menthone, and isomenthone, revealing that these compounds are the main cause of what has been called odor of isopulegol.

Since the above-mentioned purification method is costly for industrial application, the inventors have studied a more economical purification method for obtaining chemically and optically pure odorless (−)-n-isopulegol.

First of all, rectification was attempted by using, for example, a Heli-Pack distillation tower having 100 theoretical plates. It was confirmed that the thus purified (−)-n-isopulegol has a reduced and yet perceivable odor characteristic of conventionally available isopulegol and that mere distillation does not render isopulegol odorless.

As a next approach, the inventor attempted recrystallization using a variety of solvents for deep cooling and found acetone especially excellent as a deep cooling solvent.

Thus, it was found that deep cooling using acetone as a deep cooling solvent affords needle-shaped particulate crystals having a high bulk density which neatly settle to the bottom of a reaction container without adhering to the container or a stirrer. If, on the other hand, other solvents like petroleum ether are used as a solvent, it turned out that the precipitated crystals are light and fluffy needle-like crystals, which easily adhere to the reaction container or a stirrer only to attain a poor separation efficiency in the subsequent centrifugation. Therefore, recrystallization using these solvents is not efficient for removing a trace amount of the impurity.

Since the above-described deep cooling method provides crystals having high purity both chemically and optically (not less than 99.9%) through a single operation, a final product ((−)-n-isopulegol) obtained therefrom simply by centrifugal separation followed by cutting the initial fraction by means of a distillation tower is optically and chemically pure and has no odor but pleasant refreshing irritation.

Acetone is preferably used in an amount 1 to 5 times, more preferably 1.5 to 3.0 times, in terms of volume per weight, as much as the isopulegol. A minor proportion (at most 30% by weight) of acetone may be replaced with an oxygen-containing compound, such as ethyl acetate, methanol, ethanol, tetrahydrofuran, methyl ethyl ketone, dipropyl ether, and diethyl ether.

The deep cooling temperature preferably ranges from −20° to −60° C., more preferably from −25° to −50° C. After the deep cooling, the crystals are collected by centrifugation and then subjected to rectification with, for example, a 5 to 40-plate Heli-Pack distillation tower to obtain a commercial product.

(−)-n-Isopulegol to be used in the present invention preferably has as high purity as possible and is most preferably 100% pure both chemically and optically.

Menthol which can he used in the present invention is not limited, and any species prepared by known processes can be used. On an industrial scale, menthol at or above the melting point which is obtained through distillation of menthol is mixed with (−)-n-isopulegol. The thus prepared liquid l-n-menthol composition is less expensive than conventional menthol while exhibiting high quality. The composition also turned out excellent in workability and hygiene.

The isopulegol is preferably used in a proportion of 30 to 80% by weight based on the l-n-menthol composition for the following reasons.

The relationship between an isopulegol/menthol ratio and the liquid-solid state at a low temperature (0° C.) or room temperature (25° C.) was examined in Example 2 hereinafter described. As is Seen from Table 1 of Example 2, if the (−)-n-isopulegol content is less than 30% by weight, the composition tends to solidify. If the (−)-n-isopulegol content exceeds 80% by weight, the feeling of coolness of menthol would be reduced. While the isopulegol/menthol ratio may be selected arbitrarily as far as the (−)-n-isopulegol content is not lower than 30% by weight and not more than 80% by weight, it is preferable to use 45% by weight or more of (−)-n-isopulegol for preservation and/or use at low temperatures, e.g., 0° C.

The feeling of coolness on skin of menthol decreases as the proportion of menthol is reduced, but the composition essentially retains the feeling of coolness of menthol as long as it contains at least 20% by weight of menthol. Therefore, the proportion of (−)-n-isopulegol is desirably 30 to 80% by weight. When the proportion of (−)-n-isopulegol is less than 30% by weight, the resulting composition does not become liquid. However, even in this case, the feeling of coolness and mildness when applied to the mouth and skin can be increased and the bitterness can be improved as compared to the conventional case using menthol alone.

Further, in the composition of the present invention, part of (−)-n-isopulegol component may be replaced with other components. For instance, 20 to 80% by weight, preferably 40 to 60% by weight of (−)-n-isopulegol can be replaced with 3-l-n-menthoxypropane-1,2-diol as disclosed in JP-B-61-48813. Such replacement can soften both the odor of menthol and the irritation on the skin by menthol, and more increase the feeling of mildness.

The present invention thus provides a liquid l-n-menthol composition which is less expensive than conventionally available menthol and yet has an improved feeling of coolness (particularly, the bitterness is reduced) and can be used in place of conventional menthol. Besides, the liquid menthol composition of the present invention is excellent in workability and hygiene on use. That is, the present invention makes it possible to omit the flaking step that has been involved in commercialization of menthol so that various problems associated with the flaking step can be eliminated. The liquid l-n-menthol composition of the present invention is less expensive than conventional menthol, has high quality, and causes no working and hygienic problems such as scattering of powdery menthol.

Further, by replacing part of (−)-n-isopulegol component with 3-l-n-menthoxypropane-1,2-diol, the odor of menthol as well as the irritation on the skin by menthol can be softened and the feeling of mildness can be more increased.

The thus obtained liquid l-n-menthol composition can be used for various materials to which the menthol can generally be applied, such as hair cosmetics (e.g., shampoo, rinse, hair cream, hair tonic, hair conditioner, pomade, hair restoration agent, etc.), skin cosmetics (e.g., perfume, Eau de Cologne, face powder, skin cream, lipstick, liquid cream, cataplasm, cool-feeling spray, etc.), sanitary goods (e.g., body soap, facial cleansing cream, makeup remover, soap, dish detergent, detergent, softener, disinfectant detergent, deodorant detergent, aromatic, deodorizer, deodorant, maskant, sweat deodorant, bathing agent, germicide, insecticide, bleaching agent, toothpaste, mouth wash, furniture protective agent, etc.), chewing gum, hard candy, chocolate, mint tea, and tobacco to give the unique function of the composition so as to increase their commercial values.

The present invention will now be illustrated in greater detail with reference to Reference Examples and Examples, but it should be understood that the present invention is not limited thereto. Unless otherwise indicated, all the percents are by weight.

REFERENCE EXAMPLE 1 preparation of Pure (−)-n-Isopulegol (−)-n-Isopulegol which is an intermediate for the synthesis of menthol was obtained by the aforesaid Takasago process. The intermediate has a chemical purity of 97.1% and an optical purity of 97 5%e.e. ($[\alpha]_D^{25}=-20.9°$) as analyzed by GC under the following conditions and has a mild herbaceous minty fragrance.

Conditions of GC:

Column: Chiraldex CB (25 m×0.25 mm diameter), produced by Chromato Pack

He pressure: 1 kg/cm$^2$

Temperature: elevated at a rate of 2° C./min from 60° C. up to a constant temperature of 190°

Retention time for (+)-n-compound: 27.9 min

Retention time for (−)-n-compound: 28.3 min

In a 3 l-volume 4-necked container for deep cooling was put 500 g of the above-mentioned (−)-n-isopulegol, and 1500 ml of acetone was added thereto. The mixture was cooled to −40° C. in a nitrogen stream, and the precipitated solid was separated by centrifugation to obtain 367 g of crystals.

The crystals were melted and distilled in a 40-plate Heli-Pack tower to obtain 305 g of (−)-n-isopulegol (64.5° C./1 mmHg) which was found to be almost 100% pure both optically and chemically ($[\alpha]_D^{25}=-22.1°$) as analyzed by GC. The crystals were odorless and had a refreshing feeling of coolness.

EXAMPLE 1

Preparation of Liquid l-n-Menthol Composition

1) Thirty grams of the (−)-n-isopulegol prepared in Reference Example 1 and 70 g of menthol at and above the melting point which was obtained by distillation (prior to flaking) in the production of menthol were mixed to prepare a liquid l-n-menthol composition consisting of 30% of (−)-n-isopulegol and 70% of menthol.

2) Fifty grams of the (−)-n-isopulegol prepared in Reference Example 1 and 50 g of flakes of l-n-menthol were put in a 200 ml beaker, and the mixture was heated to 45° C. to melt the menthol flakes thereby to obtain a liquid l-n-menthol composition consisting of 50% of (−)-n-isopulegol and 50% of menthol.

(3) Eighty grams of the (−)-n-isopulegol prepared in Reference Example 1 and 20 g of flakes of l-n-menthol were put in a 200 ml beaker, and the mixture was heated to 45° C. to melt the menthol flakes thereby to obtain a liquid l-n-menthol composition consisting of 80% of (−)-n-isopulegol and 20% of menthol.

(4) Twenty grams of the (−)-n-isopulegol prepared in Reference Example 1, 30 g of 3-l-n-menthoxypropane-1,2-diol (manufactured by Takasago International Corporation) and 50 g of flakes of l-n-menthol (manufactured by Takasago International Corporation) were put in a 200 ml beaker, and the mixture was heated to 45° C. to melt the menthol flakes thereby to obtain a liquid l-n-menthol composition.

EXAMPLE 2

The relationship between an isopulegol/menthol ratio and the liquid-solid state at 0° C. and 25° C. was examined. The results are shown in Table 1 below.

TABLE 1

| l-n-Menthol (%) | (−)-n-Isopulegol (%) | 0° C. | 25° C. |
| --- | --- | --- | --- |
| 80 | 20 | solid | solid |
| 75 | 25 | solid | partially crystallized |
| 70 | 30 | partially crystallized | liquid |
| 60 | 40 | paritally crystallized | liquid |
| 55 | 45 | liquid | liquid |
| 50 | 50 | liquid | liquid |
| 20 | 80 | liquid | liquid |

It is seen from Table 1 that the composition containing 20% or 25% of (−)-n-isopulegol solidifies at 0° C., and the composition containing 25% of (−)-n-isopulegol crystallizes at 25° C. It was confirmed that compositions containing more than 80% of (−)-n-isopulegol had a reduced feeling of coolness of menthol.

EXAMPLE 3

Organoleptic Test

Flavor compositions for toothpaste were prepared using the liquid l-n-menthol composition prepared in Example 1-(1) according to the formulations shown in Table 2.

TABLE 2

|  | Formulation 1 | Formulation 2 |
|---|---|---|
| Peppermint oil (Madras) | 20.0 | 20.0 |
| Peppermint oil (Willamette) | 20.0 | 20.0 |
| Anethole | 10.0 | 10.0 |
| Spice base X-8396 | 6.0 | 6.0 |
| Ethyl alcohol (95%) | 11.0 | 11.0 |
| Liquid l-n-menthol composition of Example 1-(1) | 33.0 | 0.0 |
| l-n-Mentol | 0.0 | 33.0 |
| Total | 100.0 | 100.0 |

A base for evaluation of mint oil was flavored with 1% of each formulation to prepare test toothpaste. An organoleptic test of the toothpaste was conducted as follows while comparing with a flavor comprising 100% l-n-menthol.

Five specialized panel members brushed their teeth with the test toothpaste and evaluated the flavor. In order to equalize the influence of the order of use on feeling, the test was conduced twice for each sample in the order of formulation 1 - formulation 2 - formulation 2 - formulation 1.

As a result, formulation 1 had no cooling stimulation to the nose as compared with formulation 2 but was practically equal to formulation 2 in coolness felt in the mouth. There was observed almost no difference between formulations 1 and 2 in intensity and continuity of the feeling of coolness remaining in the mouth after brushing teeth. Formulation 1 had milder taste and flavor than formulation 2, covering the sharpness or roughness of peppermint oil. It was felt that formulation 1 has reduced bitterness originated in l-n-menthol as compared with formulation 2. Formulation 1 gave neither stimulation nor foreign taste originated in (−)-n-isopulegol.

All the panel members made an overall judgement from these results of evaluation that formulation 1 showed improvement over formulation 2.

EXAMPLE 4

Organoleptic Test

Fragrance compositions having a minty note for a shampoo were prepared using the liquid l-n-menthol composition prepared in Example 1-(2) according to the formulations shown in Table 3.

TABLE 3

|  | Formulation 3 | Formulation 4 |
|---|---|---|
| Coumarin | 5.0 | 5.0 |
| Ethylene brassylate | 10.0 | 10.0 |
| Camphor | 10.0 | 10.0 |
| Cyclopentadecanolide | 35.0 | 35.0 |
| Sandalwood oil | 25.0 | 25.0 |
| Cedarwood oil | 10.0 | 10.0 |
| l-Citronellol | 30.0 | 30.0 |
| Terpinyl acetate | 10.0 | 10.0 |
| Geranyl acetate | 25.0 | 25.0 |
| Terpineol | 20.0 | 20.0 |
| Isobornyl acetate | 20.0 | 20.0 |
| Linalyl acetate | 15.0 | 15.0 |

TABLE 3-continued

|  | Formulation 3 | Formulation 4 |
|---|---|---|
| Linalool | 85.0 | 85.0 |
| Tetrahydrolinalool | 40.0 | 40.0 |
| Dihydromyrcenol | 25.0 | 25.0 |
| Lavandin | 75.0 | 75.0 |
| Rosemary oil | 30.0 | 30.0 |
| Orange terpene | 45.0 | 45.0 |
| Dipropylene glycol | 35.0 | 35.0 |
| Liquid l-n-menthol composition of Example 1-(2) | 450.0 | 0.0 |
| l-n-Menthol | 0.0 | 450.0 |
| Total | 1000.0 | 1000.0 |

A shampoo perfumed with 1% of each formulation was prepared and evaluated by an organoleptic test by 10 panel members.

As a result, 7 out of 10 preferred formulation 3 to formulation 4, mentioning that the former, while having less cooling stimulation, felt fresher and gave a milder fragrance. Two made substantially equal judgements, and one preferred formulation 4 to formulation 3.

EXAMPLE 5

Mouth wash formulation 5 shown below was prepared using the liquid l-n-menthol composition obtained in Example 1-(3).

| Mouth Wash Formulation 5 |  |
|---|---|
| Japanese pharmacopeia ethanol (95%) | 7.00 |
| Polyoxyethylene hardened castor oil (Nikkol HCO60) | 2.00 |
| Mouth wash flavor | 0.20 |
| Purified glycerin | 10.00 |
| Sodium benzoate | 0.05 |
| Sodium saccharin | 0.01 |
| Liquid l-n-menthol composition prepared in Example 1-(3) | 0.05 |
| Purified water | 80.69 |
| Total | 100.00 |

As a result of an organoleptic test, all the panel members judged the mouth wash excellent in freshness and feeling of coolness.

EXAMPLE 6

To a shampoo base formulation 6 shown below, the liquid l-n-menthol composition prepared in Example 1-(4) was added in an amount of 0.5% to obtain Product of the present invention. Similarly, l-n-menthol flakes were added to the formulation 6 in the same amount to obtain Comparative product.

| Shampoo base formulation 6 |  |
|---|---|
| Purified water | 42.830 |
| O-[2-hydroxy-3-(trimethylammonio)propyl] hydroxyethyl cellulose chloride | 0.600 |
| Polyoxyethylene laurylether sodium sulfate (3E.O.)(25%) | 40.000 |
| Disodium sulfosuccinic acid polyoxyethylene lauroyl ethanol amide (5E.O.) | 5.000 |
| 2-Alkyl-N-carboxymethyl-N-hydroxyethyl-imidazoliniumbetaine (40%) | 5.000 |
| Coconut oil fatty acid diethanolamide | 4.000 |

-continued

| Shampoo base formulation 6 | |
|---|---|
| Glycerin | 0.100 |
| Ethylene glycol distearate | 1.500 |
| Citric acid | 0.220 |
| Potassium chloride | 0.300 |
| Methyl para-hydroxybenzoate | 0.200 |
| Propyl para-hydroxybenzoate | 0.100 |
| Ethyl para-hydroxybenzoate | 0.100 |
| Edetic acid tetrasodium | 0.050 |
| Total | 100.000 |

Each 1 ml of Product of the present invention and Comparative Product was applied to both arms of 12 panelists and foamed with water of about 40° C. to evaluate the smell of the composition and the effect on the skin to provide cooling feel during use. Further, the foams were washed away and the arms were wiped with towel completely and then subjected to evaluation of the smell and the effect on the skin to provide cooling feel were evaluated the five minutes later. The results on relative evaluation are shown in Table 4.

While the invention has been described in detail and with reference to specific examples thereof, it will be apparent to one skilled in the art that various changes and modifications can be made therein without departing from the spirit and scope thereof.

What is claimed is:

1. A liquid l-n-menthol composition containing 30 to 80% by weight of (−)-n-isopulegol.

2. A liquid a-n-menthol composition as claimed in claim 1, wherein part of the (−)-n-isopulegol component is replaced with 3-l-n-menthoxypropane-1,2-diol.

3. A liquid l-n-menthol composition as claimed in claim 1, wherein said (−)-n-isopulegol is one purified by deep cooling in a solvent mainly comprising acetone.

4. A liquid l-n-menthol composition as claimed in claim 2, wherein said (−)-n-isopulegol is one purified by deep cooling in a solvent mainly comprising acetone.

5. A process for preparing a liquid l-n-menthol composition comprising mixing 20 to 70 parts by weight of liquid menthol at a temperature of not lower than 42° C. with 30 to 80 parts by weight of (−)-n-isopulegol.

6. A process for preparing a liquid l-n-menthol composition as claimed in claim 5, wherein part of the (−)-n-isopulegol component is replaced with 3-l-n-menthoxypropane-1,2-diol.

TABLE 4

| | Comparative Product | | | Almost | Product of the Invention | | | |
|---|---|---|---|---|---|---|---|---|
| Items of evaluation | Pretty strong 3 | Strong 2 | Slightly strong 1 | the same 0 | Slightly strong −1 | Strong −2 | Pretty strong −3 | Average score |
| Strength of smell | | | | | | | | |
| During washing | 1 | 1 | 9 | 0 | 0 | 1 | 0 | 1.00 |
| 5 min. later the wash | 0 | 0 | 3 | 8 | 1 | 0 | 0 | 0.17 |
| Mild feel of smell | | | | | | | | |
| During washing | 0 | 0 | 1 | 1 | 10 | 0 | 0 | −0.75 |
| 5 min. later the wash | 0 | 0 | 0 | 11 | 1 | 0 | 0 | −0.08 |
| Cool feel on the skin | | | | | | | | |
| During washing | 0 | 0 | 6 | 4 | 2 | 0 | 0 | 0.33 |
| 5 min. later the wash | 0 | 0 | 6 | 4 | 2 | 0 | 0 | 0.33 |
| Irritation on the skin | | | | | | | | |
| During washing | 0 | 0 | 6 | 5 | 1 | 0 | 0 | 0.42 |
| 5 min. later the wash | 0 | 0 | 5 | 7 | 0 | 0 | 0 | 0.42 |

As is clear from the above results, the smell and the irritation of menthol can be reduced by mixing (−)-n-isopulegol with 3-l-n-methoxypropane-1,2-diol to provide milder feeling.

* * * * *